United States Patent
Higuchi et al.

(10) Patent No.: US 6,551,289 B1
(45) Date of Patent: Apr. 22, 2003

(54) OUTER NEEDLE OF ANESTHETIC NEEDLE ASSEMBLY FOR EPIDURAL

(75) Inventors: Akio Higuchi, Tokyo (JP); Hayato Hyugaji, Tokyo (JP)

(73) Assignee: Dr. Japan Co., Ltd., Tokyo (JP)

( * ) Notice: Subject to any disclaimer, the term of this patent is extended or adjusted under 35 U.S.C. 154(b) by 0 days.

(21) Appl. No.: 09/830,273

(22) PCT Filed: Sep. 27, 1999

(86) PCT No.: PCT/JP99/05235

§ 371 (c)(1),
(2), (4) Date: Apr. 25, 2001

(87) PCT Pub. No.: WO01/19435

PCT Pub. Date: Mar. 22, 2001

(30) Foreign Application Priority Data

Sep. 14, 1999 (JP) ............................................ 11-260348

(51) Int. Cl.[7] .................................................. A61M 5/32

(52) U.S. Cl. ...................................................... 604/272

(58) Field of Search ................................ 604/272, 273, 604/274

(56) References Cited

U.S. PATENT DOCUMENTS

| | | | | |
|---|---|---|---|---|
| 2,716,983 A | * | 9/1955 | Windischman et al. ...... 604/274 |
| 2,830,587 A | * | 4/1958 | Everett ......................... 604/272 |
| 5,290,267 A | * | 3/1994 | Zimmermann ............... 604/272 |
| 5,295,980 A | * | 3/1994 | Ersek ............................ 604/272 |
| 5,536,259 A | * | 7/1996 | Utterberg ...................... 604/272 |
| 5,575,780 A | * | 11/1996 | Saito ............................. 604/264 |

FOREIGN PATENT DOCUMENTS

| | | |
|---|---|---|
| JP | 284390 | 9/1953 |
| JP | 3930253 | 12/1964 |
| JP | 9149936 | 6/1997 |

* cited by examiner

*Primary Examiner*—Gene Mancene
*Assistant Examiner*—Patrick Buechner
(74) *Attorney, Agent, or Firm*—Birch, Stewart, Kolasch & Birch, LLP

(57) ABSTRACT

A outer needle of an anesthetic needle assembly to be injected into an epidural area, has a distal end which is cut and bent to form an annular cutting edge. The distal end is gently bent so that an anesthetic needle having a forward end can slide readily out of the annular cutting edge. The annular cutting edge has a wave-like configuration with an extended circular or rectangular annulus with round corners and outwardly expanded sides.

8 Claims, 3 Drawing Sheets

OUTER NEEDLE OF ANESTHETIC NEEDLE ASSEMBLY FOR EPIDURAL

This application is the national phase under 35 U.S.C. §371 of PCT International Application No. PCT/JP99/05253 which has an International filing date of Sep. 27, 1999, which designated the United States of America and was not published in English.

TECHNICAL FIELD

The present invention relates to an outer needle of an anesthetic needle assembly to be injected into an epidural area of the body.

BACKGROUND OF THE INVENTION

The anesthetic needle assembly is composed of outer and inner needles, of which the inner needle is taken out of the outer needle after the needle assembly is injected into the epidural area of a patient. Then, the outer needle is used as a guide for insertion of a catheter or anesthetic needle.

The outer needle is known as a spinal needle that is made of a stainless steel tube, of which the bevel cut end is bent to form a distal end of the outer needle. The distal end has an annular cutting edge forming an elliptic, planar opening. The annular cutting edge has a relatively sharp cutting angle, for example, 30 degrees at an outer frontal corner part thereof.

As seen in FIG. 5, the known outer needle 8 has a distal end with a somewhat sharp curve. When the catheter or anesthetic needle 10 is inserted into the outer needle 8, it has the forward end thereof butting the inner surface of the distal end 9 of the outer needle 8 in the steeply inclined direction with the result that it cannot pass through the distal end 9 without meeting with a large frictional resistance. This leads to a disadvantage that it is not easy for the catheter or anesthetic needle to have the forward end to project out of the annular cutting edge 18 of the outer needle 8.

As seen in FIGS. 6 and 7, the other outer needle 19 has been proposed to have a distal end 21 with a relatively gentle curve, in order to solve the aforementioned disadvantage. The outer needle 19 allows the catheter or anesthetic needle 20 to easily project the forward end from the annular cutting edge 22, because there is a fair chance for the forward end to pass through the distal end without butting the inner surface of the distal end 21. Although the catheter or anesthetic needle 20 is inserted in the outer needle 19 in a manner that the forward end thereof knocks the inner surface of the distal end 21, it buts the inner surface of the distal end 19 in the gently inclined direction with the result that the forward end can pass through the distal end 19 and project from the annular cutting edge 22 without meeting with a large frictional resistance. However, the outer needle 19 has the problem that the annular edge 22 is apt to wound the epidural membrane when injected into the epidural area. The other problem is that the catheter is sometimes caught and damaged by the annular edge 22 when it is drawn out from the outer needle 19.

Thus, the annular cutting edge 22 has a sharp cutting angle at the outer frontal corner part 23 thereof defined by the major axis and the mother line of the outer needle 19 with the result that the outer needle 19 is apt to wound the epidural membrane. When the distal end 21 with a relatively gentle curve is injected in the epidural area, the outer frontal corner part 23 with a sharp cutting angle touches the epidural membrane in the near vertical direction. The annular cutting edge 22 also has a sharp cutting angle at the inner frontal corner part 24 thereof defined by the major axis and the mother line of the outer needle 19 with the result that the outer needle 19 sometimes damages the catheter. When the catheter is drawn from the outer needle, it approaches the rear narrow wedge-shaped portion of the elliptic planar opening surrounded by the annular cutting edge 22 whereby the catheter contacts the inner frontal corner part 24 with a sharp cutting angle.

SUMMARY OF THE INVENTION

The present invention as claimed is intended to solve the problems described above and provide an outer needle of an anesthetic needle assembly for epidural use. The needle is improved as follow:

1. It has an annular cutting edge in which the outer frontal corner part is prevented from injuring the epidural membrane when injected into the epidural area.
2. It has an annular cutting edge in which the inner frontal corner part is prevented from catching or damaging the catheter being drawn out of the outer needle through the rear portion of the annular cutting edge.
3. It allows an anesthetic needle to project from the forward end portion thereof, i.e., from the annular cutting edge, with ease.

The anesthetic needle assembly to be injected into the epidural area of a patient has an outer needle that is mostly made of a stainless steel tube. According to the present invention, the outer needle has a distal end portion bent in a manner that, when an anesthetic needle has the forward end thereof contacted with the inner surface of the distal end portion of the outer needle, the front end slides out of the annular cutting edge of the outer needle through the inner surface of the distal end. The annular cutting edge has an opening with major and minor axes and is composed of bifurcated forward convex surfaces and bifurcated rear concave surfaces with respect to a plane including the major and minor axes. The outer needle has dull cutting angles at the outer and inner frontal corner parts of the waved annular cutting edge in comparison with the known outer needle having sharp cutting angles at the outer and inner frontal corner parts of the planar annular cutting edge.

In preference, the annular cutting edge has such bifurcate convex and concave surfaces that are symmetrical with respect to a plane including the major axis and perpendicular to the minor axis to form a smooth continuous wave surface. But, it is also possible that each of the convex and concave surfaces is composed of discontinuous planar or curved surface portions and the convex and concave surfaces are crossly or stepwise joined to one another.

In preference, the respective cutting angles at the outer and inner frontal corner parts of the annular cutting edge are in a range of 60 to 90 degrees that are twice or more as large as those of the known planar annular cutting edge.

In preference, the annular cutting edge has a top view of an extended circle or oblong with four round corners and two outwardly curved long sides, in order to prevent the catheter from being wedged in the rear portion of the annular cutting edge when the catheter is drawn out. The catheter contacts the inner frontal corner part of the annular cutting edge without receiving any damage because the corner part has a dull cutting angle.

Further scope of applicability of the present invention will become apparent from the detailed description given hereinafter. However, it should be understood that the detailed description and specific examples, while indicating preferred embodiments of the invention, are given by way of illustration only, since various changes and modifications

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

THE BEST MODE OF CARRYING OUT THE INVENTION

Figure 1:
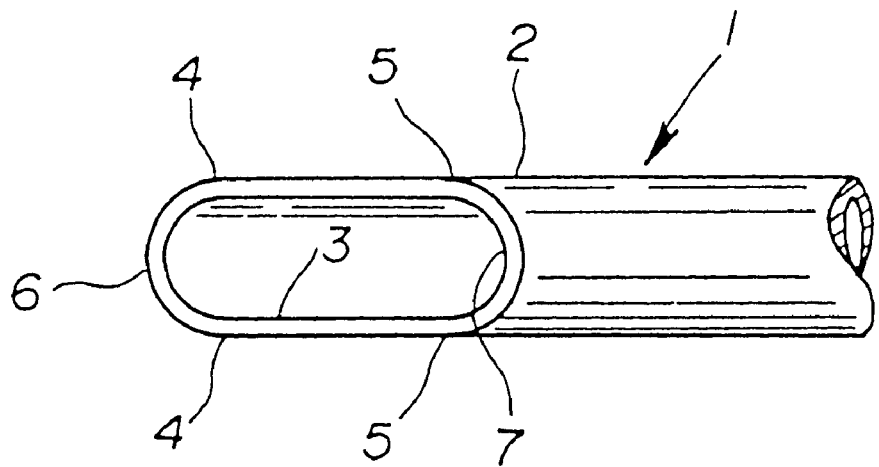
FIG. 1 is a plan view of the relevant portion of an outer needle according to a first embodiment of the present invention.

The present invention will be more clearly understood with reference to the embodiments as shown in the drawings.

Figure 2:
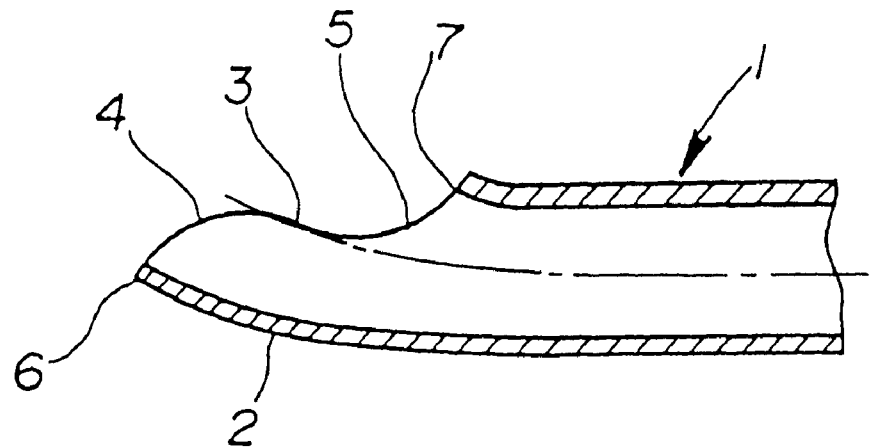
FIG. 2 is a longitudinal cross-section of the relevant portion of the outer needle of FIG. 1.

As seen in FIGS. 1 and 2 respectively showing a plan and a longitudinal cross-section of the relevant portion of an outer needle according to a first embodiment of the present invention, the outer needle 1 is made of a fine stainless tube of which the one end is bent and cut by means of electrical discharge machining or the like to form a distal end. The outer needle 1 has a distal end 2 thereof with a relatively gentle curvature so that a forward end of an anesthetic needle does not stop but slides on the inner surface of the distal end 2, when the inner surface of the distal end is contacted with the forward end of the anesthetic needle passing through the outer needle. The distal end of the outer needle 1 is less curved than that of the known outer needles. The annular cutting edge 3 of the outer needle 1 has a convex, concave plane of which the outer major and minor axes are similar to those of known outer needles having the same outer diameter.

The annular cutting edge 3 is formed in the forward half thereof with a bifurcated convex surface 4 out of a plane including the outer major and minor axes of the annular cutting edge 3 and in the rear half with a bifurcated concave surface 5 in the same plane including outer major and minor axes of the annular cutting edge 3. The bifurcate convex and concave surfaces 4, 5 are symmetrical with respect to a plane including the outer major axis and perpendicular to the outer minor axis of the annular cutting edge 3.

The annular cutting edge 3 has an outer frontal corner part 6 with a cutting angle similar to a crossing angle between the convex surface 4 and the longitudinal line of the under outer surface of the outer needle 1 in the plane including the outer major axis and perpendicular to the outer minor axis, and an inner frontal corner part 7 with a cutting angle similar to a crossing angle between the concave surface 5 and the longitudinal line of the upper inner surface of the outer needle 1 in the plane including the outer major axis and perpendicular to the outer minor axis. The convex surface 4 is so shaped that the outer frontal corner part 6 has a cutting angle of 60 degrees or more. The cutting angle is at least twice as large as that of the known outer needle. The concave surface 5 is also shaped so that the inner frontal corner part 7 has a cutting angle of 60 degrees or more. The cutting angle is also at least twice as large as that of the known outer needle. The convex and concave surfaces are continuously, smoothly joined to each other.

When the outer needle 1 has the annular cutting edge 3 injected into the epidural area of a patient, the distal end 2 has the outer frontal corner part 6 contacted with the dural membrane in a nearly perpendicular direction because of being less curved. However, the outer frontal corner part 6 tends to introduce no damage to the dural membrane because its cutting angle is too large to inflict a substantial wound.

The annular cutting edge 3 has convex and concave surfaces and a plane view of a somewhat extended circular annulus. When a non-shown catheter is drawn from the outer needle 1, it passes through the annular cutting edge 3 without being wedged in the rearward portion of which the inner frontal corner part is gently curved. The catheter receives no damage from the inner frontal corner part 7 of the annular cutting edge 3 when it contacts the inner frontal corner part 7 with the relatively large, dull cutting angle.

Figure 3:
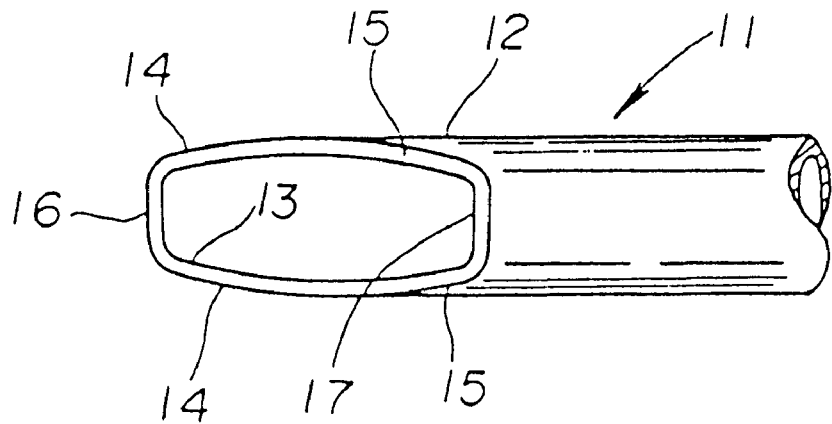
FIG. 3 is a similar view to FIG. 1, showing the relevant portion of an outer needle according to a second embodiment of the present invention.
Figure 4:
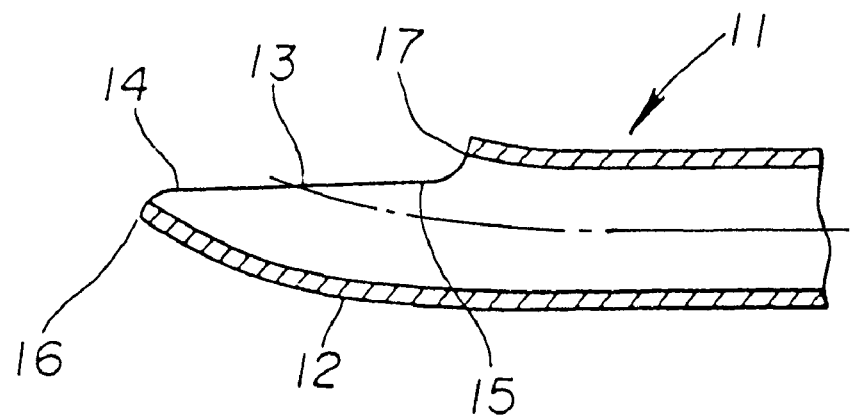
FIG. 4 is a similar view to FIG. 2, showing the second embodiment.
Figure 5:
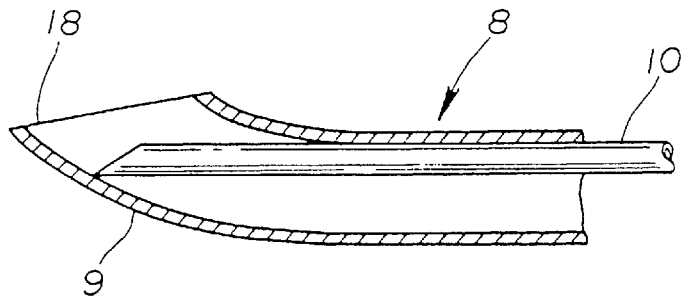
FIG. 5 is a longitudinal cross-section of a relevant portion of a known outer needle.
Figure 6:
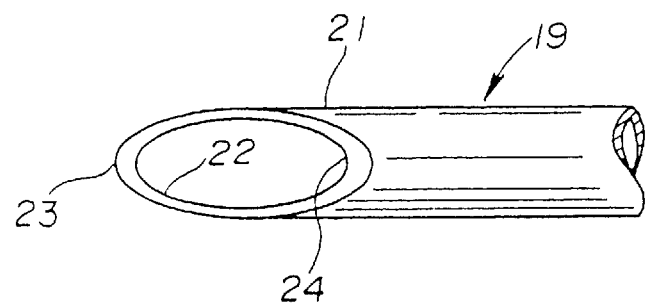
FIG. 6 is a plane view of the relevant portion of the known outer needle.
Figure 7:
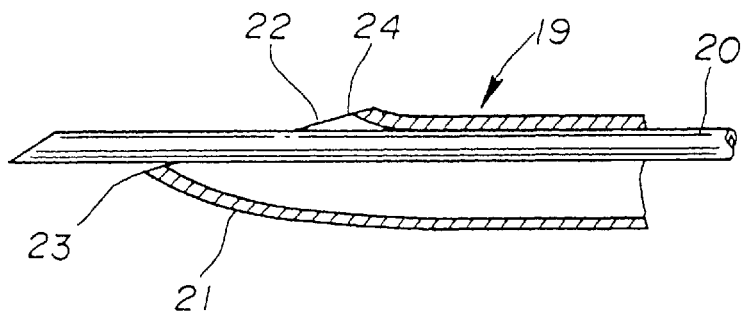
FIG. 7 is a similar view to FIG. 5, showing the known outer needle.

A second embodiment according to the present invention is shown in FIGS. 3 and 4, respectively illustrating a plane and a longitudinal section of the distal end. The outer needle 11 is also made of a stainless steel tube of a predetermined length, which is cut and bent by means of electrical discharge machining or the like in the same manner as the previous embodiment. The annular cutting edge 13 has a plane view showing a somewhat rectangular annulus with round corners and outwardly curved sides. The annular cutting edge 13 also has a pair of outer major and minor axes similar to those of the known outer needle having the same outer diameter.

As the annular cutting edge 13 is viewed in the direction parallel to the minor axis, it is formed in the forward half with a convex surface 14 which starts perpendicularly from the longitudinal line of the under outer surface of the outer needle 11, turns with a small curvature and extends to the center of the distal end 12 in which the convex surface 14 is joined to the concave surface 15 of the rearward portion of the annular cutting edge 13. The concave surface 15 extends in the same direction, turns with a small curvature and terminates perpendicular to the longitudinal line of the upper outer surface of the outer needle 11. The outer frontal corner part 16 of the annular cutting edge 13 has a cutting angle of 90 degrees that is unable to make a cutting action. This means that the outer needle 11 introduces no wound to the dural membrane when it is injected into the epidural area. As seen in a plane view showing the annular cutting edge 13, the inner frontal corner part 17 is so flat that the catheter passes through without being wedged in the rearward portion of the annular cutting edge 13. Even if the catheter contacts the inner frontal corner part 17 when drawn out from the annular cutting edge 13, it is free from receiving a wound. The reason for this is that the inner frontal corner part 17 has a cutting angle of 90 degrees which makes it unable to make a cutting action.

From the foregoing, the outer needle according to the present invention comprises a distal end gently curved and a waved annular cutting edge composed of bifurcated forward convex and rearward concave surfaces with respect to a plane including the outer major and minor axes, in a manner that the outer and inner frontal corner parts have the respective relatively large or dull cutting angle as compared with the known planar annular cutting edge. Furthermore, the annular cutting edge has a plan view showing an extended circular or rectangular annulus with round corners and outwardly curved sides. The needle of the present invention offers many advantages one of which is that the distal end allows an anesthetic needle to have its forward end sliding out of the distal end with ease, even if an anesthetic needle is inserted in the outer needle to have its forward end contacted with the inner surface of the distal end. Another advantage is that a catheter passes through the annular cutting edge without being wedged in the rear portion thereof when it is drawn from the outer needle. A further advantage is that the dural membrane receives no wound with the outer frontal corner part of the annular cutting edge when the outer needle is injected into the epidural area. A still further advantage is that the catheter is free from being damaged by the inner frontal corner part of the annular cutting edge when it is drawn out of the outer needle.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An outer needle of an anesthetic needle assembly to be injected into an epidural area comprising a distal end formed with an annular cutting edge, wherein the distal end is gently curved, and the annular cutting edge has a forward half portion in the form of bifurcated convex surfaces over a plane including outer major and minor axes of said annular cutting edge, said annular cutting edge having an outer frontal corner part with a cutting angle that is larger than a crossing angle between said major axis and a longitudinal line of an outer surface of said outer needle in a plane including said major axis and perpendicular to said minor axis.

2. The outer needle as claimed in claim 1, wherein said inner frontal corner part has a rectangular cutting angle.

3. The outer needle as claimed in claim 1, wherein said annular cutting edge has a rearward half portion in the form of bifurcated concave surfaces under said plane including outer major and minor axes of said annular cutting edge, said annular cutting edge having an inner frontal corner part with a cutting angle that is larger than a crossing angle between said major axis and a longitudinal line of an upper inner surface of said outer needle in a plane including said major axis and perpendicular to said minor axis.

4. The outer needle as claimed in claim 3, wherein said inner frontal corner part has a rectangular cutting angle.

5. The outer needle as claimed in claim 3, wherein the cutting angle is at least twice as larger as that of the known outer needle.

6. The outer needle as claimed in claim 3, wherein either or both of said bifurcate convex and concave surfaces of said annular cutting edge are symmetrical to each other with respect to a plane including said outer major axis and perpendicular to said minor axis of said annular cutting edge.

7. The outer needle as claimed in claim 6, wherein said annular cutting edge has an extended circular annulus.

8. The outer needle as claimed in claim 6, wherein said annular cutting edge has a rectangular annulus with round corners and outwardly curved sides.

* * * * *